US008158065B2

(12) United States Patent
Trentzsch et al.

(10) Patent No.: US 8,158,065 B2
(45) Date of Patent: Apr. 17, 2012

(54) IN SITU MONITORING OF METAL CONTAMINATION DURING MICROSTRUCTURE PROCESSING

(75) Inventors: Martin Trentzsch, Dresden (DE); Stephan Kronholz, Dresden (DE); Rolf Stephan, Dresden (DE)

(73) Assignee: Advanced Micro Devices, Inc., Austin, TX (US)

( * ) Notice: Subject to any disclaimer, the term of this patent is extended or adjusted under 35 U.S.C. 154(b) by 224 days.

(21) Appl. No.: 12/507,986

(22) Filed: Jul. 23, 2009

(65) Prior Publication Data
US 2010/0077839 A1   Apr. 1, 2010

(30) Foreign Application Priority Data

Sep. 30, 2008 (DE) .......................... 10 2008 049 774

(51) Int. Cl.
*G01N 35/00* (2006.01)
*G01R 31/26* (2006.01)
*H01L 21/66* (2006.01)
*G01N 29/02* (2006.01)

(52) U.S. Cl. .............. 422/119; 438/14; 438/16; 438/17; 73/23.2

(58) Field of Classification Search .................. 422/119; 438/14, 16, 17; 73/31.03, 61.42, 23.2, 53.01, 73/61.41; 156/345.24
See application file for complete search history.

(56) References Cited

U.S. PATENT DOCUMENTS

| 5,369,495 | A | * | 11/1994 | Lagowski ...................... 356/418 |
| 5,405,492 | A | * | 4/1995 | Moslehi ......................... 438/694 |
| 5,474,648 | A | | 12/1995 | Patrick et al. .............. 156/627.1 |
| 5,528,648 | A | * | 6/1996 | Komatsu et al. ................. 378/45 |
| 5,583,282 | A | * | 12/1996 | Tom .............................. 73/31.03 |
| 5,636,256 | A | * | 6/1997 | Matumura et al. .............. 378/45 |
| 5,910,011 | A | * | 6/1999 | Cruse .............................. 438/16 |
| 5,930,586 | A | | 7/1999 | Jain et al. ......................... 438/14 |
| 6,427,093 | B1 | * | 7/2002 | Toprac .......................... 700/121 |
| 6,759,255 | B2 | * | 7/2004 | Xu et al. .......................... 438/14 |
| 7,084,466 | B1 | * | 8/2006 | Lee et al. ...................... 257/414 |
| 2005/0173375 | A1 | | 8/2005 | Mitrovic et al. ................ 216/60 |
| 2005/0276378 | A1 | * | 12/2005 | Ito .................................. 378/70 |

FOREIGN PATENT DOCUMENTS

| DE | 691 17 480 T2 | 12/1991 |
| DE | 694 03 593 T2 | 8/1994 |
| DE | 102006035596 A1 | 1/2008 |
| JP | 04012251 A | 1/1992 |

OTHER PUBLICATIONS

Translation of Official Communication from German Patent Office for German Patent Application No. 10 2008 049 774.6 dated Oct. 26, 2010.

* cited by examiner

*Primary Examiner* — Walter D Griffin
*Assistant Examiner* — Natasha Young
(74) *Attorney, Agent, or Firm* — Williams, Morgan & Amerson

(57) ABSTRACT

By providing a tool internal sensor device in a process tool in a semiconductor facility, metal contamination may be monitored in situ, thereby avoiding or at least significantly reducing the requirement for sophisticated sample preparation techniques, such as vapor phase decomposition tests in combination with subsequent analysis procedures. Thus, a full time inspection of process tools may be accomplished.

18 Claims, 2 Drawing Sheets

IN SITU MONITORING OF METAL CONTAMINATION DURING MICROSTRUCTURE PROCESSING

BACKGROUND OF THE INVENTION

1. Field of the Invention

Generally, the present disclosure relates to the field of fabricating microstructure devices, and, more particularly, to techniques for enhancing product yield by reducing the defect rate caused by metal contamination at several process stages during the formation of complex microstructures, such as integrated circuits and the like.

2. Description of the Related Art

Today's global market forces manufacturers of mass products to offer high quality products at a low price. It is thus important to improve yield and process efficiency to minimize production costs. This holds especially true in the field of fabricating microstructures having a complex configuration, such as advanced integrated circuits, since here it is essential to combine cutting edge technology with mass production techniques. It is, therefore, the goal of manufacturers of microstructures to reduce the consumption of raw materials and consumables while at the same time improve process tool utilization. The latter aspect is especially important since, in modern semiconductor facilities, equipment is required, which is extremely cost intensive and represents the dominant part of the total production costs. Consequently, high tool utilization, in combination with a high product yield, i.e., with a high ratio of good devices and faulty devices, results in increased profitability.

Complex microstructures, such as integrated circuits, are typically manufactured in automated or semi-automated facilities, thereby passing through a large number of process and metrology steps to complete the device. The number and the type of process steps and metrology steps a semiconductor device has to go through depends on the specifics of the device to be fabricated. For example, a usual process flow for an integrated circuit, which may be considered as a representative of a complex microstructure, may include a plurality of photolithography steps to image a circuit pattern for a specific device layer into a resist layer, which is subsequently patterned to form a resist mask used in further processes for forming device features in the device layer under consideration by, for example, etch, implant, deposition, polish processes and the like. Thus, layer after layer, a plurality of process steps are performed based on a specific lithographic mask set for the various layers of the specified device. For instance, a sophisticated CPU requires several hundred process steps, each of which has to be carried out within specified process margins to fulfill the specifications for the device under consideration. Since many of these processes are very critical, a plurality of metrology steps have to be performed to efficiently control the process flow. Typical metrology processes may include the measurement of layer thickness, the determination of dimensions of critical features, such as the gate length of transistors, the measurement of dopant profiles, the number, the size and the type of defects, and finally the electrical characteristics, which may represent the contribution of a plurality of process stages and which may finally decide whether a device is an operational device or a faulty device.

In a semiconductor facility, a plurality of different product types are usually manufactured at the same time, such as memory chips of different design and storage capacity, CPUs of different design and operating speed and the like, wherein the number of different product types may even reach one hundred and more in production lines for manufacturing ASICs (application specific ICs). Since each of the different product types may require a specific process flow, different mask sets for the lithography, specific settings in the various process tools, such as deposition tools, etch tools, implantation tools, chemical mechanical polishing CMP) tools, metrology tools and the like may be necessary. Consequently, the process flow in the facility may be very complex, since many re-entrant processes, i.e., a repeated use of the same process tools at different manufacturing stages of a specific type of product, and many predictable and non-predictable events may occur during the manufacturing processes and the various metrology processes.

Due to the continuous shrinkage of feature sizes of the circuit elements, such as the gate length of field effect transistors and the like, a plurality of tightly set process margins and specifications have to be fulfilled during the complex manufacturing process in order to obtain the required functionality, speed and reliability of the final semiconductor devices. A significant deviation from these tightly set specifications, which may be caused by any type of process fluctuations, contaminations and the like, may have a direct influence on the finally obtained device parameters, such as overall performance of circuit elements, the time to electrical breakdown, failure caused by electromigration and the like. For example, metal contaminations created in corresponding dielectric and/or semiconductive areas of semiconductor devices have been a concern during recent decades in the microelectronic industry. For instance, the presence of metal contaminations in semiconductor areas may result in additional electronic state in the band gap of the corresponding semiconductor material, thereby, for instance, reducing lifetime of minority charge carriers and the like. Furthermore, the incorporation of metal contaminations into sensitive dielectric areas, such as gate dielectric materials, may considerably alter the dielectric behavior of these materials, thereby contributing to increased leakage currents. Corresponding effects are even further exacerbated in highly sophisticated semiconductor devices in which corresponding dielectric materials approach physical limits, wherein only a few atomic layers may be provided for sophisticated dielectric materials. Similarly, the incorporation of undesired metal species in doped semiconductor areas may result in modified junction behavior, thereby also contributing to increased diode leakage currents, which in turn may also contribute to dynamic and static leakage currents. For this reason, great efforts have been made in order to monitor the degree of metal contamination throughout the entire manufacturing process flow, in particular as highly conductive metals such as copper are increasingly used in sophisticated semiconductor devices. As is well known, copper readily diffuses in a plurality of dielectric materials, such as silicon dioxide and the like, and also in silicon, wherein even minute amounts of copper may have a significant influence on the overall device performance, as explained above.

The problem of metal contamination may further be exacerbated by the fact that any process tools, such as process tools for performing wet chemical treatment, such as etching, resist strip and the like, may be used at several stages of the entire process flow in view of enhancing overall process tool utilization, as discussed above. For example, at many stages of the overall manufacturing flow, resist material may have to be applied, patterned and used as a mask for etch processes, implantation processes and the like, wherein a subsequent removal of the resist mask may be accomplished on the basis of plasma-based or wet chemical-based etch processes. Similarly, in many stages of the overall process flow, sophisticated cleaning processes, for instance for removing organic contaminations, particles and the like, may have to be performed, for instance on the basis of wet chemical treatments, while in other cases surface areas of the substrates may have to be patterned on the basis of wet chemical etch chemistries. Also, in this case, the same process tool may be used at several very different stages of the overall manufacturing flow, thereby contributing to an increased probability of introducing undesired metal species into the corresponding process chambers and/or process liquids used for establishing an appropriate process ambient. In order to monitor the status of the various process tools and thus of the substrates to be processed in these tools, corresponding measurements may be performed on a regular basis in order to identify metal species that may be present in the various process chambers and process liquids. For this purpose, sophisticated monitoring techniques have been established, such as TXRF (total reflectance x-ray fluorescence), ICPMS (inductively coupled mass spectrometry) and the like. For example, in a TXRF metrology process, a smooth surface portion of a test substrate may be exposed to a probing x-ray beam that is incident on a small angle, thereby resulting in a substantially total reflectance of the incoming beam. On the other hand, atoms in the vicinity of the surface may be excited by the x-ray beam, which may cause a respective secondary radiation that is detected by a solid body detector, thereby enabling characteristic spectra to enable detection of type and amount of characteristic metal species. In order to further enhance sensitivity of this measurement technique, the sample surface may be appropriately prepared by vapor phase decomposition in which the sample surface may be treated on the basis of hydrofluoric acid, thereby dissolving any surface oxide of the sample wafer together with corresponding metal contaminants. The resulting droplets that are condensed on the sample surface may then be further analyzed by TXRF, thereby obtaining enhanced sensitivity. In other cases, the resulting droplets may be evaporated and may be analyzed by spectrometry, wherein even further enhanced sensitivity may be achieved, while, however, efforts with respect to preparing the sample and preparing the overall measurement procedure may be increased compared to the above-explained x-ray measurement techniques. In this manner, an overview of the different metals, such as cadmium, cer, aluminum, lead, copper and the like, may be obtained for the corresponding process liquids used in the process tools. For obtaining relative measurement results with respect to the metal contamination, the vapor phase decomposition process in combination with the subsequent actual analysis technique may require high efforts in terms of delay for obtaining the measurement results and also in terms of production costs due to the requirement of sample wafers and significant resources with respect to process engineers.

The present disclosure is directed to various methods and devices that may avoid, or at least reduce, the effects of one or more of the problems identified above.

SUMMARY OF THE INVENTION

The following presents a simplified summary of the invention in order to provide a basic understanding of some aspects of the invention. This summary is not an exhaustive overview of the invention. It is not intended to identify key or critical elements of the invention or to delineate the scope of the invention. Its sole purpose is to present some concepts in a simplified form as a prelude to the more detailed description that is discussed later.

Generally, the present disclosure relates to techniques and systems in which information with respect to metal contamination of process tools used for the fabrication of microstructure devices, such as semiconductor devices, may be gathered "in situ" by providing a tool internal sensor system. That is, in illustrated aspects disclosed herein, an appropriately designed sensor system, or at least a corresponding sensor device or sensitive portion thereof, may be positioned so as to allow a process ambient and/or a corresponding process liquid or other precursor material, such as process gases to be used for establishing the process ambient, to interact with the sensor system or a portion thereof in order to obtain an appropriate response indicative of the degree of metal contamination. For example, one or more process liquids used in process tools configured to process microstructure devices or semiconductor devices may be monitored on the basis of a tool internal sensor system by detecting a variation of, for instance, an inductance, a capacitance and the like, caused by a corresponding variation of degree of metal species incorporated in the corresponding process liquids. In other illustrative aspects disclosed herein, any other moderately fast analysis techniques may be provided in combination with the tool internal sensor system, thereby also providing the possibility of generating information with respect to metal contamination with reduced time delay and significantly less effort in terms of human resources.

One illustrative process tool disclosed herein comprises a process chamber configured to receive and hold in place a substrate for forming microstructure devices, wherein the process chamber is further configured to establish a chemically reactive process ambient. The process tool further comprises a sensor device positioned to detect metal contamination in the process ambient and/or a precursor material used to establish the process ambient. Finally, the process tool further comprises a control unit connected to the sensor device and being configured to provide an indication correlated to a degree of metal contamination of the process ambient and/or the precursor material.

One illustrative method disclosed herein relates to monitoring metal contamination in a semiconductor process tool. The method comprises exposing a sensor device in the semiconductor process tool to at least one of a process ambient and one or more process fluids used to establish the process ambient. Furthermore, the method comprises obtaining a sensor signal from the sensor device, wherein the sensor signal is indicative of a degree of metal contamination of the process ambient and/or the one or more process fluids. Furthermore, the degree of metal contamination is indicated on the basis of the sensor signal.

A still further illustrative method disclosed herein comprises processing a plurality of substrates in a process tool provided in a manufacturing environment that is configured to form microstructure devices above the plurality of substrates. Furthermore, the method comprises obtaining process status information from the process tool from a tool internal sensor system, wherein the process status information is correlated to a degree of metal contamination of the plurality of substrates caused by the process tool.

BRIEF DESCRIPTION OF THE DRAWINGS

The disclosure may be understood by reference to the following description taken in conjunction with the accompanying drawings, in which like reference numerals identify like elements, and in which.

Figure 1A:
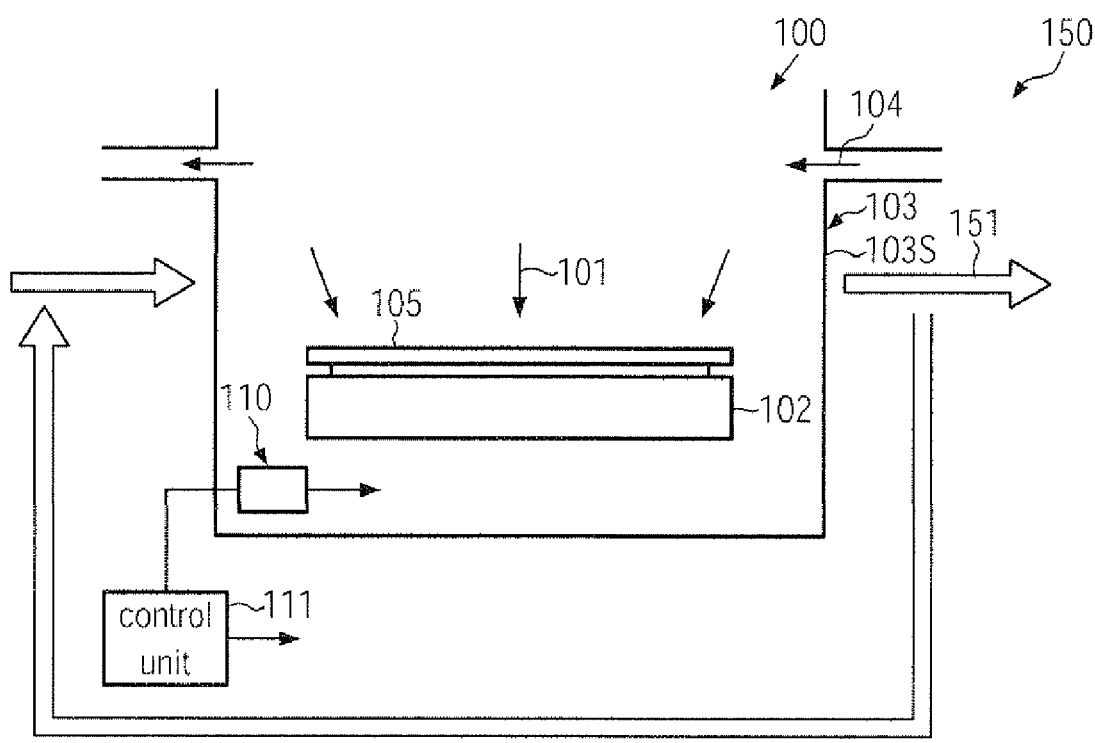
FIG. 1a schematically illustrates a process tool for processing microstructure devices, such as semiconductor devices, comprising an in situ sensor system for obtaining information on metal contamination in the process tool, according to illustrative embodiments.

While the subject matter disclosed herein is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION

Various illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present subject matter will now be described with reference to the attached figures. Various structures, systems and devices are schematically depicted in the drawings for purposes of explanation only and so as to not obscure the present disclosure with details that are well known to those skilled in the art. Nevertheless, the attached drawings are included to describe and explain illustrative examples of the present disclosure. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase.

Generally, the subject matter disclosed herein provides systems and methods for obtaining information on the degree of metal contamination during the processing of substrates for forming microstructure devices in a highly efficient manner by providing a sensor system or at least a sensor device within a process tool. For this purpose, a sensor device, or at least a portion thereof, may be positioned such that an interaction of the process ambient in the process tool, such as a wet chemical process ambient, a plasma assisted gaseous process ambient and the like, may take place, for instance, during processing of substrates or at least during a dedicated tool state in order to provide information on the degree of metal contamination with reduced delay and less required operator interaction, thereby providing the possibility of monitoring the contamination state of the process tool with a desired degree of time resolution. In other illustrative embodiments, in addition to monitoring the status of metal contamination of the process ambient, specific process fluids, such as liquids and the like, may be monitored with respect to metal contamination, thereby also providing valuable information with respect to the overall contamination state of the process tool and thus the corresponding substrates processed in the tool during the various manufacturing stages. The tool internal sensor system may be provided in any appropriate configuration, which provides the desired interaction between the process ambient and/or the process fluids and a sensitive portion, at least one characteristic of which may vary depending on the amount and/or the type of metal contaminants. For example, electromagnetic characteristics of sensor components, such as capacitance, inductance, a combination thereof, etc., may change in relation to the presence of metal contaminants, thereby enabling an efficient detection of the corresponding electrical characteristic, for instance, by monitoring the frequency response of a resonant circuit and the like. For example, the tool internal sensor device may comprise a capacitor having at least a sensor which may influence the overall capacitance of the sensor capacitor upon contact with the process ambient and/or the corresponding process fluids. In other cases, upon interaction with the process ambient and/or the process fluids, the inductance of an inductive element may change, which may be detected on the basis of an appropriately designed evaluation circuit, for instance by evaluating the frequency response of the inductive element, for instance in terms of a varying phase, resonance, amplitude and the like.

In other illustrative embodiments disclosed herein, well-established measurement techniques, for instance TXRF techniques, may be used in order to probe an appropriately positioned sensor surface with an x-ray beam. In this case, the response of the sensor surface may be detected by an appropriate detector, wherein respective measurement results may be obtained within several minutes, which may still be compatible with an in situ measurement technique. For example, the corresponding sensor surface may be temporarily exposed to the process ambient while processing one or more substrates and the probing of the sensor surface may be performed after isolating the sensor surface from the process ambient. Hence, also in this case, in situ measurement results may be obtained with low delay, wherein the corresponding measurement accuracy may be sufficient to monitor the advance of a contamination status of the process tool under consideration.

Consequently, an inline setup for monitoring the metal contamination in sophisticated semiconductor process tools, such as wet chemical process tools and the like, may be accomplished, thereby providing substantially continuous monitoring while at the same time reducing production costs by avoiding complex vapor phase decomposition techniques. A corresponding monitoring of the metal contamination of process tools over extended time periods may be highly advantageous in the context of complex manufacturing flows, in which the same process tool may be used during various manufacturing stages since, in these situations, the probability of creating metal contaminations may be moderately high, wherein the substantially continuous monitoring of the contamination status may even allow for an estimation of possible contamination sources. Hence, respective contamination prone process steps may be identified more efficiently, thereby even further contributing to enhanced process efficiency, reduced production costs and device reliability.

FIG. 1a schematically illustrates a portion of a manufacturing environment 150, which is to be understood as an environment including a plurality of process tools of which, for convenience, only a single process tool 100 is illustrated, wherein a plurality of process tools may be operated on the basis of corresponding process recipes in order to produce microstructure devices, such as semiconductor devices. For example, the manufacturing environment 150 may represent a production line for producing integrated circuits in which circuit elements such as transistors and the like may be incorporated having critical dimensions of approximately 50 nm and less. Hence, in the manufacturing environment 150, an overall manufacturing flow 151 may be performed in which substrates, such as semiconductor wafers and the like, may be passed through a plurality of process tools, such as lithography tools, etch tools, implantation tools, deposition tools and the like, so as to obtain the microstructure devices in a desired state of completeness, as is also explained above. In the manufacturing flow 151, the process tool 100 may represent a process tool which may be used at several points of the flow 151 so that the corresponding substrate to be processed may represent microstructure devices at different stages of completeness and may thus have experienced different process steps and may have come into contact with different materials. As previously explained, in sophisticated semiconductor devices, increasingly, new materials may be provided, for instance with respect to gate dielectrics, sophisticated metallization systems and the like, so that the potential for introducing contaminating species and also the potential for creating contaminated sensitive materials may be significantly increased so that a thorough monitoring of contamination mechanism, in particular in re-entrant process tools, such as the process tool 100, may contribute to increased overall process efficiency and finally to product reliability. In some illustrative embodiments, the process tool 100 may represent a tool for creating a reactive process ambient 101, for instance on the basis of process liquids, such as acids, base liquids and the like. For example, the process tool 100 may represent a wet chemical cleaning or etch tool, in which the reactive ambient 101 may be established on the basis of reactive process liquids for etching materials, removing resist materials and the like. For instance, the reactive ambient 101 may be established on the basis of liquids, which may be used for the processing of a plurality of substrates, wherein increasingly metal contaminants may accumulate, for instance due to contact to substrates at different manufacturing stages which may contaminate components of the process tool 100, such as a substrate holder 102 or surface areas 103S of a process chamber 103 and the like. Thus, upon delivering a process fluid 104 to the process chamber 103, a corresponding contamination may occur, for instance during maintaining the process fluid 104 within the process chamber 103 and/or upon contacting respective components of the tool 100, wherein these metal contaminations may finally deposit on a substrate 105 that may be exposed to the ambient 101.

Furthermore, the process tool 100 may comprise a tool internal sensor device 110 which may be configured to interact with the process ambient 101 and/or the process fluid 104 in order to provide corresponding information with respect to the degree of metal contamination of the process tool 100. For this purpose, the tool internal sensor device 110 may be connected to a control unit 111, which may be configured to at least obtain a signal from the device 110 and to provide an indication correlated with a degree of contamination of the tool 100. For example, the tool internal sensor device 110, which may also be referred to as an in situ sensor device, may have at least one characteristic that may vary with the amount and/or the type of metal species present in the ambient 101 and/or the fluid 104. For this purpose, a sensitive surface area may be provided in the device 110 that may be positioned so as to be at least temporarily in contact with the ambient 101 and/or the fluid 104. In other cases, the sensor device 110 may comprise an appropriately designed system of conduits so as to establish a circulatory system, wherein at least a portion of the conduit system may be used as a "detector" for obtaining information on the degree of metal contamination of the process fluid circulating in the corresponding circulatory system. For this purpose, process fluid from a corresponding reservoir within the process chamber 101 may be pumped through the circulatory system of the device 110, thereby using a portion of the conduit system as a "metal detector," which may be accomplished by well-established techniques, such as metal detection systems as may also be used in food production and the like.

In the operation of the process tool 100 in the environment 150, the substrate 105 may be received in the chamber 103, i.e., on the substrate holder 102 and, depending on the specified process recipe, the process ambient 101 may be established. Prior to, during and/or after processing the substrate 105, the tool internal sensor system 110 may also be exposed to the ambient 101 and/or the process fluid 104 so that corresponding contamination related information may be obtained by using the control unit 111. Since the tool internal sensor system 110 may allow a substantially "continuous" monitoring or at least a monitoring with a fine time resolution, a variation of the metal contamination status of the tool 100 may be obtained for various substrates at different manufacturing stages, thereby enabling a correlation of metal contamination with the corresponding manufacturing stage. Hence, significant sources of metal contamination, i.e., corresponding manufacturing stages of the substrates 105, may be identified by determining a prominent increase of metal contamination after processing a plurality of substrates 105 corresponding to the manufacturing stage under consideration.

Figure 1B:
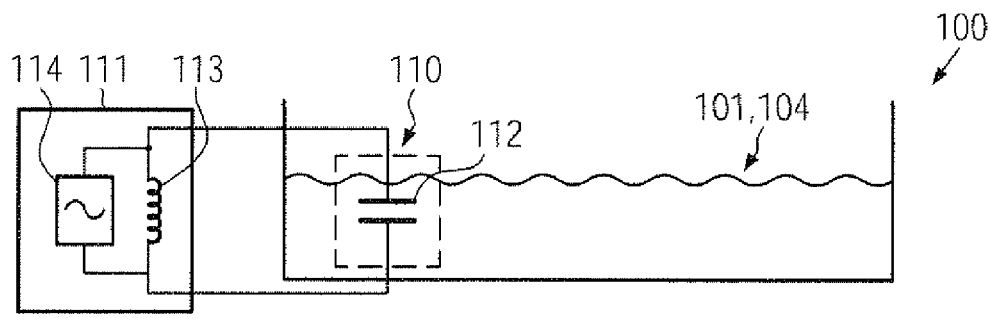
FIG. 1b schematically illustrates the process tool with an in situ sensor device configured to change a frequency response depending on the degree of metal contamination, for instance by changing a capacitance thereof, according to illustrative embodiments.

FIG. 1b schematically illustrates the process tool 100 according to illustrative embodiments in which the tool internal sensor device 110 may comprise a capacitive element 112 whose capacitance may vary upon interaction with the process ambient 101 and/or the fluid 104, depending on the degree of metal species present. For instance, the capacitive element 112 may be positioned such that the process fluid 104 may act as a capacitor dielectric in which a varying composition, i.e., a varying degree of metal species, may result in a corresponding varying permittivity and thus capacitance of the element 112. Thus, upon driving the capacitive element 112 on the basis of an appropriate signal, which may include a plurality of different frequency components, the response of the element 112 may be detected by the control unit 111 and may be used for determining the currently obtained permittivity and thus capacitance of the element 112. For example, the control unit 111 may comprise an inductive component 113 which may form, in combination with the capacitive element 112, a resonant circuit, the resonant behavior of which may thus depend on the capacitance of the element 112 and thus on the permittivity and hence on the degree of metal contamination of the process fluid 104. During operation of the tool 100, at any appropriate stage, that is, prior to receiving the substrate 105 during the processing of the substrate 105, or after processing the substrate 105, the element 112 may be brought into contact with the fluid 104, at least for a specified time period, and the control unit 111 may supply the frequency dependent signal. For instance, an oscillator 114 may be coupled to the element 112 to excite the resonant circuit formed by the components 113, 112 with different frequencies, wherein one or more of the phase, the amplitude, the impedance and the like may be monitored by the control unit 111 in order to monitor the frequency dependent response of the element 112. It should be appreciated that appropriate reference data may be generated, for instance on the basis of the element 112, when provided in a well-defined state with respect to metal contamination and the like. Hence, a required measurement variable, which may indicate the change in permittivity of the capacitor dielectric and thus of the degree of metal contamination, may be monitored and may be used as an indication of the degree of metal contamination.

It should be appreciated that the capacitive element 112 may also be used in combination with electronic circuitry, such as an oscillator for storing charge on the capacitor 112 at different frequencies, since typically the permittivity of a process liquid 104 may depend on the frequency with which the capacitor 112 may be operated and thus respective results may be obtained for a plurality of different frequencies, thereby enhancing the overall accuracy of the measurement results. Due to the increased accuracy obtained on the basis of the plurality of frequency components, subtle variations of the permittivity at the various frequencies may thus be determined with increased accuracy, thereby also enhancing the accuracy of the evaluation of the degree of metal contamination. In other illustrative embodiments, the component 112 may be "probed" by a high number of frequency components simultaneously, for instance by supplying a delta-like pulse and analyzing the frequency response of the component 112, for instance by sophisticated digital signal processing techniques and the like, thereby also obtaining a high degree of sensitivity of the device 110 with respect to metal contamination.

Figure 1C:
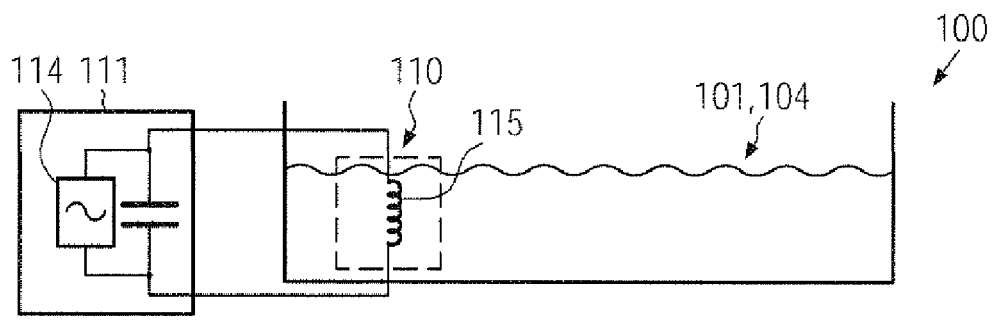
FIG. 1c schematically illustrates the process tool in which the in situ sensor system may comprise a variable inductive element for obtaining a frequency response dependent on the degree of metal contamination, according to still further illustrative embodiments.

FIG. 1c schematically illustrates the process tool 100 according to further illustrative embodiments in which the tool internal sensor device 110 may comprise an active component 115, wherein the permeability of the inductive component 115 may change upon interaction with the process ambient 101 and/or the process liquid 104. Thus, also in this case, the control unit 111 may be appropriately configured to drive the component 115 with appropriate signals in order to detect the frequency dependent response of the component 115, which in turn depends on the change of permeability and thus on the presence of respective metal species. For example, the inductive component 115 may be a part of a resonant circuit, the oscillating behavior of which may therefore be dependent on the degree of metal contamination and may efficiently be detected by the control unit 111, similarly as is also described with reference to FIG. 1b.

It should be appreciated that the tool internal sensor devices 110 as described with reference to FIGS. 1a-1c may be positioned such as to be in permanent contact, at least during an operational mode of the tool 100, while in other cases the device 110 or at least a portion thereof may be brought into contact with the ambient 101 and/or the process fluid 104 for a predetermined time interval, for instance for interacting and measuring, while thereafter the device 110 may be brought into a defined position or state so as to enable a reference measurement in order to reduce interferences and noise. For instance, the sensor device 110 may be isolated from the ambient 101 and/or the process fluid 104, thereby providing different conditions, which may represent well-defined reference conditions. To this end, for instance, contact to the process fluid 104 when provided in the form of a liquid may be discontinued, thereby frequently reducing the overall permittivity if, for instance, the capacitive element 112 is considered, which may enable a measurement of the component 112 in a state without influence of metal contamination, thereby providing an appropriate reference signal, which may appropriately be superimposed to the previously obtained signal or to a signal that may be obtained when the component 112 is in contact with the process liquid 104. In this manner, the device 110 may act as a reference assembly, which may enable a significant reduction of any device specific drifts or other fluctuations, which may otherwise be superimposed on the actual measurement results.

Figure 1D:
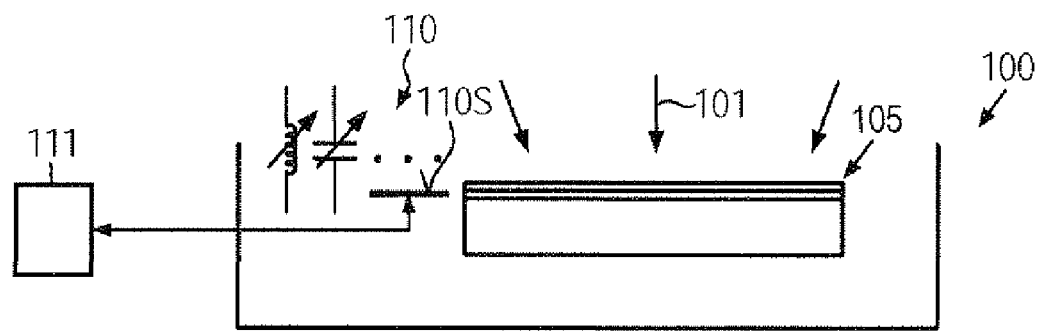
FIG. 1d schematically illustrates the process tool according to still further illustrative embodiments in which a sensor surface may be positioned to interact with a process ambient in order to obtain information on the degree of metal contamination.

FIG. 1d schematically illustrates the process tool 100 according to still further illustrative embodiments in which the tool internal sensor device 110 may comprise a sensor surface 110S, which may be appropriately configured to interact with the ambient 101, which may be a gaseous ambient, such as a plasma assisted etch ambient and the like, wherein the presence of a metal species may provide a modification of the sensor surface 110S. For instance, the surface 110S may have formed thereon or therein an appropriate conductive structure acting as an inductance or a capacitor, or both, wherein a deposition or incorporation of a metal species may result in a variation of the corresponding electronic or magnetic characteristics, as previously described with reference to FIGS. 1b and 1c. Consequently, by appropriately driving the device 110 by means of the control unit 111, an estimation of the degree of metal contamination may be obtained, wherein similar process conditions may be achieved for the sensor surface 110S compared to the substrate 105 so that the actual contamination status of the substrate 105 may be estimated on the basis of the status of the surface 110S. Thus, if any means for removing the surface contaminants from the sensor surface 110S may not be provided within the process tool 100, the time progression of the accumulated metal contamination may be monitored by means of the device 110, wherein the accumulated metal contamination may represent the conditions at the substrate 105 with a high degree of authenticity, since the surface 110S may be positioned close to the corresponding substrate 105 processed in the tool 100. Moreover, the corresponding surface configuration of the surface 110S may be designed such that even minute deposition of metal species may provide a significant change of the corresponding electric or magnetic characteristics so that metal contamination in gaseous ambients may also be monitored.

Figure 1E:
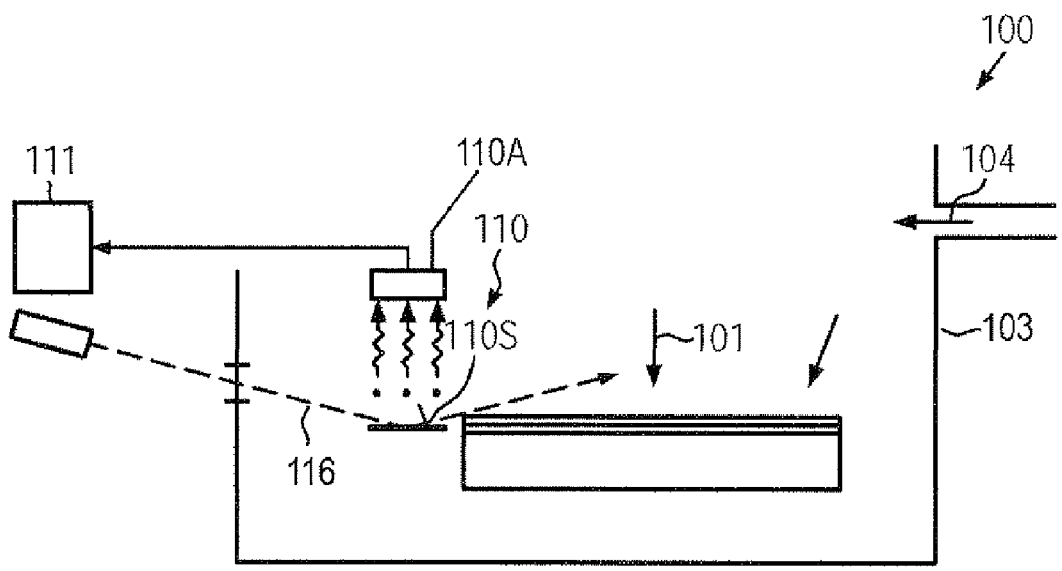
FIG. 1e schematically illustrates the process tool including the in situ sensor device having a sensor surface that may be probed by an x-ray beam, according to still further illustrative embodiments.

FIG. 1e schematically illustrates the process tool 100 according to further illustrative embodiments in which the tool internal sensor device 110 may comprise the surface 110S, which may be appropriately conditioned to allow probing of the surface 110S by an appropriate probing beam 116. For example, the sensor surface 110S may be a silicon surface or any other appropriate smooth material layer that may be more or less inert with respect to a process ambient 101 and/or the process fluids 104 in order to provide substantially constant surface conditions for a plurality of measurements. Furthermore, the sensor device 110 may comprise a detector 110A, for instance a solid body detector that is positioned at any appropriate location within the process chamber 103 or outside thereof in order to receive radiation emitted by at least a portion of the sensor surface 110S upon reaction with the probing beam 116. For example, the probing beam 116 may be provided in the form of an x-ray beam that may be incident on the surface 110S at a very low angle of incidence, such as 0.1-0.5 degrees, thereby obtaining the condition for total reflection, which may allow obtaining an appropriate response of atoms in and on the surface 110S, as previously explained with reference to the TXRF technique. Thus, the corresponding signals of the detector 110A may be supplied to the control unit 111, which may thus determine the amount and/or type of metal contaminants incorporated in the surface 110S. As previously explained, corresponding TXRF measurements may be performed within a few minutes or less, so that a corresponding degree of contamination may be determined during the processing of only several substrates 105, thereby providing the desired delay of the measurement results. It should be appreciated that, if required, the actual measurement process, i.e., supplying the probing beam 116 and obtaining the corresponding response by the detector 110A, may be performed under well-defined conditions, for instance by isolating the device 110 from the ambient 101, which may be accomplished by closing a shutter and the like. In other cases, the sensor surface 110S may temporarily be brought into contact with a process liquid, for instance by dipping the surface 110S into the liquid, and thereafter the actual measurement process may be performed, for instance possibly in combination with surface preparation and the like, which may be performed isolated from the ambient 101, thereby substantially not negatively influencing overall process throughput of the tool 100.

Figure 1F:
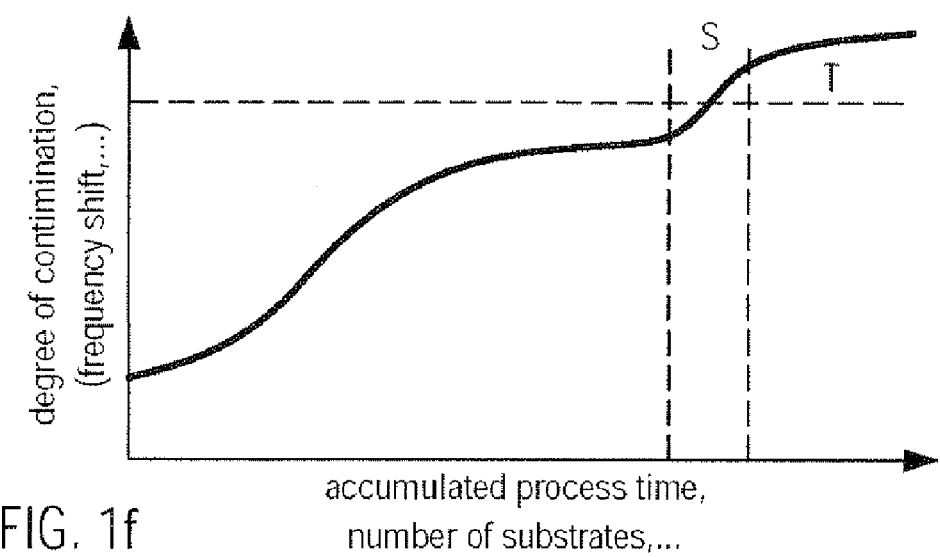
FIG. 1f schematically illustrates a graph representing the response of an in situ sensor system over an extended process time period, according to illustrative embodiments.

FIG. 1f schematically illustrates the progression of measurement results obtained by the tool internal sensor device 110 during a specific process time interval. As illustrated, the horizontal axis may represent a measure of the accumulated process time, such as the number of substrates processed in the tool 100 and the like. The vertical axis may represent an indication for the degree of metal contamination, for instance a shift of resonance frequency, an intensity of a specific portion of a spectrum and the like. As illustrated, during an increase of the accumulated process time, the degree of metal contamination may also increase since, for instance, the plurality of contaminated substrates may be processed in the process tool under consideration. Due to the substantially "continuous" monitoring of the degree of contamination, an appropriate threshold, indicated as T, may be defined in advance and may indicate a maximum allowable degree of metal contamination of the process tool under consideration. Upon approaching or exceeding the threshold T, appropriate measures may be taken, for instance shutting off the corresponding process chamber for maintenance and the like in order to remove metal contaminants prior to using the process tool for further processing of substrates. It should be appreciated that any other strategies may be used on the basis of the determined degree of metal contamination so as to enhance overall process efficiency. As previously indicated, respective sources of increased contamination may be identified, for instance, on the basis of pronounced increases, as is for instance indicated by the interval S, when the corresponding increase is correlated with a processing of specified substrates having a specific manufacturing stage. For example, if the process tool under consideration may be used for wet chemical resist removal manufacturing stages, a significant increase according to the time interval S may indicate a high degree of metal contamination prior to the corresponding resist removal process when substantially substrates have been processed during the interval S that correspond to this specific resist removal process.

As a result, the present disclosure provides process tools and methods in which the meal contamination of a process tool may be monitored in a highly efficient manner by a tool internal or in situ sensor device without requiring sophisticated and complex sample preparation procedures, such as vapor phase decomposition tests and the like. Due to the in situ nature of the measurements, a substantially continuous monitoring may be achieved, i.e., measurement results may be obtained at reduced measurement times compared to conventional strategies and with reduced delay, so that a "full time inspection" of the process tools may be established. Thus, in particular, process tools that are used for processing substrates of different manufacturing stages may be monitored with high reliability while nevertheless providing tightly set process margins with respect to metal contaminations of the substrates at each of the various manufacturing stages. Thus, increased flexibility in designing manufacturing flows and scheduling substrates in complex semiconductor facilities may be obtained since tool dedication may be relaxed due to the "continuous" metal contamination monitoring.

The particular embodiments disclosed above are illustrative only, as the invention may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A process tool, comprising:
   a process chamber configured to receive and hold in place a substrate for forming microstructure devices, said process chamber being further configured to establish a chemically reactive process ambient;
   a sensor device positioned to detect metal contamination in at least one of said process ambient and a precursor material used to establish said process ambient; and
   a control unit connected to said sensor device and being configured to provide an indication correlated to a degree of metal contamination of said at least one of said process ambient and a precursor material, wherein said sensor device is configured to be operated on the basis of drive signal including a plurality of frequency components and to provide a frequency dependent response that is related to said degree of metal contamination.

2. The process tool of claim 1, wherein said control unit comprises a resonant circuit for at least one of driving said sensor device and obtaining said frequency dependent response.

3. The process tool of claim 1, wherein said sensor device comprises an inductive component, an inductance of which is related to said degree of metal contamination.

4. The process tool of claim 1, wherein said sensor device comprises a capacitive element, a capacitance of which is related to said degree of metal contamination.

5. A process tool, comprising:
- a process chamber configured to receive and hold in place a substrate for forming microstructure devices, said process chamber being further configured to establish a chemically reactive process ambient;
- a sensor device positioned to detect metal contamination in at least one of said process ambient and a precursor material used to establish said process ambient, wherein said sensor device comprises a sensor surface and wherein said sensor surface is configured to be probed at least temporarily by a probing beam; and
- a control unit connected to said sensor device and being configured to provide an indication correlated to a degree of metal contamination of said at least one of said process ambient and a precursor material.

6. The process tool of claim 5, wherein said sensor device further comprises a detector positioned to receive a response from said sensor surface when probed by said probing beam.

7. The process tool of claim 6, wherein said probing beam comprises x-ray radiation.

8. A method of monitoring metal contamination in a semiconductor process tool, the method comprising:
- exposing a sensor device in said semiconductor process tool to at least one of a process ambient and one or more process fluids used to establish said process ambient;
- obtaining a sensor signal from said sensor device, said sensor signal being indicative of a degree of metal contamination of said at least one of process ambient and one or more process fluids; and
- indicating said degree of metal contamination on the basis of said sensor signal.

9. The method of claim 8, further comprising processing one or more substrates in said semiconductor process tool when exposing said sensor device to at least one of said process ambient and said one or more process fluids.

10. The method of claim 8, wherein said sensor device is exposed to at least one process liquid used to establish said process ambient.

11. The method of claim 8, wherein said sensor device is exposed to at least one process gas used to establish said process ambient.

12. The method of claim 10, wherein obtaining said sensor signal comprises detecting a variation of at least one of an inductance and a capacitance of said sensor device.

13. The method of claim 8, wherein obtaining said sensor signal comprises temporarily probing a sensor surface of said sensor device with an x-ray beam and detecting a response of said sensor surface to said x-ray beam.

14. A method, comprising:
- processing a plurality of substrates in a process tool provided in a manufacturing environment, said manufacturing environment configured to form microstructure devices above said plurality of substrates; and
- obtaining process status information from said process tool from a tool internal sensor system, said process status information being correlated to a degree of metal contamination of said plurality of substrates caused by said process tool.

15. The method of claim 14, wherein processing said plurality of substrates comprises establishing a wet chemical process ambient.

16. The method of claim 14, wherein processing said plurality of substrates comprises establishing a plasma based process ambient.

17. The method of claim 14, wherein obtaining said process status information comprises contacting a sensor device with at least one process liquid and detecting a change of at least one of an inductance and a capacitance of said sensor device.

18. The method of claim 14, wherein obtaining said process status information comprises probing a sensor surface of said sensor system by an x-ray beam and detecting a response of said sensor surface.

\* \* \* \* \*